US008845664B2

(12) United States Patent
Pedrick et al.

(10) Patent No.: US 8,845,664 B2
(45) Date of Patent: Sep. 30, 2014

(54) UTERINE CLAMP

(76) Inventors: Clayton B. Pedrick, Houston, TX (US);
Grant Schaffner, Cincinnati, OH (US)

(*) Notice: Subject to any disclaimer, the term of this patent is extended or adjusted under 35 U.S.C. 154(b) by 529 days.

(21) Appl. No.: 12/983,975

(22) Filed: Jan. 4, 2011

(65) Prior Publication Data
US 2012/0172898 A1  Jul. 5, 2012

(51) Int. Cl.
  *A61B 17/42* (2006.01)
  *A61B 17/08* (2006.01)
  *A61B 17/12* (2006.01)
  *A61B 17/122* (2006.01)

(52) U.S. Cl.
  CPC .......... *A61B 17/42* (2013.01); *A61B 2017/4216* (2013.01); *A61B 2017/12004* (2013.01); *A61B 17/122* (2013.01)
  USPC .......................................... 606/157; 606/119

(58) Field of Classification Search
  CPC .. A61B 17/122; A61B 17/4241; A61B 17/42; A61B 2017/12004
  USPC ........... 128/830; 600/37, 16, 18, 31; 606/157, 606/119, 151, 193, 158; 601/153; 602/13; 292/121, 122, 219, 220, 292
  See application file for complete search history.

(56) References Cited

U.S. PATENT DOCUMENTS

| | | | |
|---|---|---|---|
| 2,826,193 A * | 3/1958 | Vineberg | 601/153 |
| 3,091,242 A * | 5/1963 | Johnson, Jr. et al. | 607/105 |
| 4,428,351 A | 1/1984 | Davis | |
| 4,536,893 A * | 8/1985 | Parravicini | 623/3.21 |
| 5,057,117 A | 10/1991 | Atweh | |
| 5,186,711 A | 2/1993 | Epstein | |
| 5,236,437 A * | 8/1993 | Wilk et al. | 606/207 |
| 5,697,942 A * | 12/1997 | Palti | 606/151 |
| 5,848,962 A * | 12/1998 | Feindt et al. | 600/16 |
| 6,036,706 A * | 3/2000 | Morejohn et al. | 606/158 |
| 6,762,928 B2 * | 7/2004 | Lo | 361/679.58 |
| 6,808,483 B1 * | 10/2004 | Ortiz et al. | 600/16 |
| 7,420,799 B2 * | 9/2008 | Wang | 361/679.27 |
| 7,969,731 B2 * | 6/2011 | Yang et al. | 361/679.55 |
| 2006/0170223 A1 * | 8/2006 | Homer et al. | 292/102 |

FOREIGN PATENT DOCUMENTS

GB       2441112 A    2/2008
WO  PCT/EG2008/00009 A  8/2009

* cited by examiner

*Primary Examiner* — Gregory Anderson
*Assistant Examiner* — Christopher L Templeton
(74) *Attorney, Agent, or Firm* — Tim L. Burgess, P.C.

(57) ABSTRACT

A uterine clamp for stemming or stopping bleeding of a hemorrhagic uterus. A pair of inflatable bladders are nested in a pair of rigid shells shaped and sized to fit the anterior and posterior of a uterus without impinging on the uterine horn on placement of the shells nesting the bladders in mirrored spaced opposition to one another in front of and behind the uterus and the broad ligament supporting the uterus. At least one latch on an upper end of one shell and at least one latch catch in the upper end of the other shell provide an interlock for releasably interlocking the opposed shells in front of and behind the broad ligament anteriorly and posteriorly against the uterus for inflation of the bladders to compress the uterus to stem or stop hemorrhage.

20 Claims, 10 Drawing Sheets

UTERINE CLAMP

STATEMENT REGARDING FEDERALLY SPONSORED RESEARCH AND DEVELOPMENT

Not Applicable

BACKGROUND OF THE DISCLOSURE

1. Field of Disclosure

The present invention generally relates to the field of medical devices which exert pressure on an internal organ to control bleeding.

2. Background

Post Partum hemorrhage (PPH) is a major cause of morbidity and mortality in the United States and worldwide. Postpartum hemorrhage can lead to massive blood transfusion and an emergency hysterectomy. The World Health Organization estimates that 127,000 deaths occur annually secondary to PPH. A recent study in the US estimates that PPH complicates 2.7% of all deliveries. Attempts at stopping uterine bleeding have taken many forms over the years of varying insult to the organ and patient. A current countermeasure to uterine hemorrhage is the Bakri Postpartum Balloon. The Balloon is inserted into the uterus via the vaginal canal and is inflated to fill the uterine cavity. The objective is to control bleeding. However, the Balloon is not always effective because the uterus is a distensible tissue. A need remains for a device that allows a surgeon to quickly and easily perform this important and often life saving function.

BRIEF DESCRIPTION OF THE DRAWINGS

In the following detailed description of exemplary embodiments, reference is made to the accompanying drawings, which form a part hereof and in which are shown by way of illustration examples of exemplary embodiments with which the invention may be practiced. The drawings are not necessarily to scale. Certain features of the invention may be shown exaggerated in scale or in somewhat schematic form and some details of conventional elements may not be shown in the interest of clarity and conciseness. Referring to the drawings.

DETAILED DESCRIPTION OF EMBODIMENTS

Figure 1:
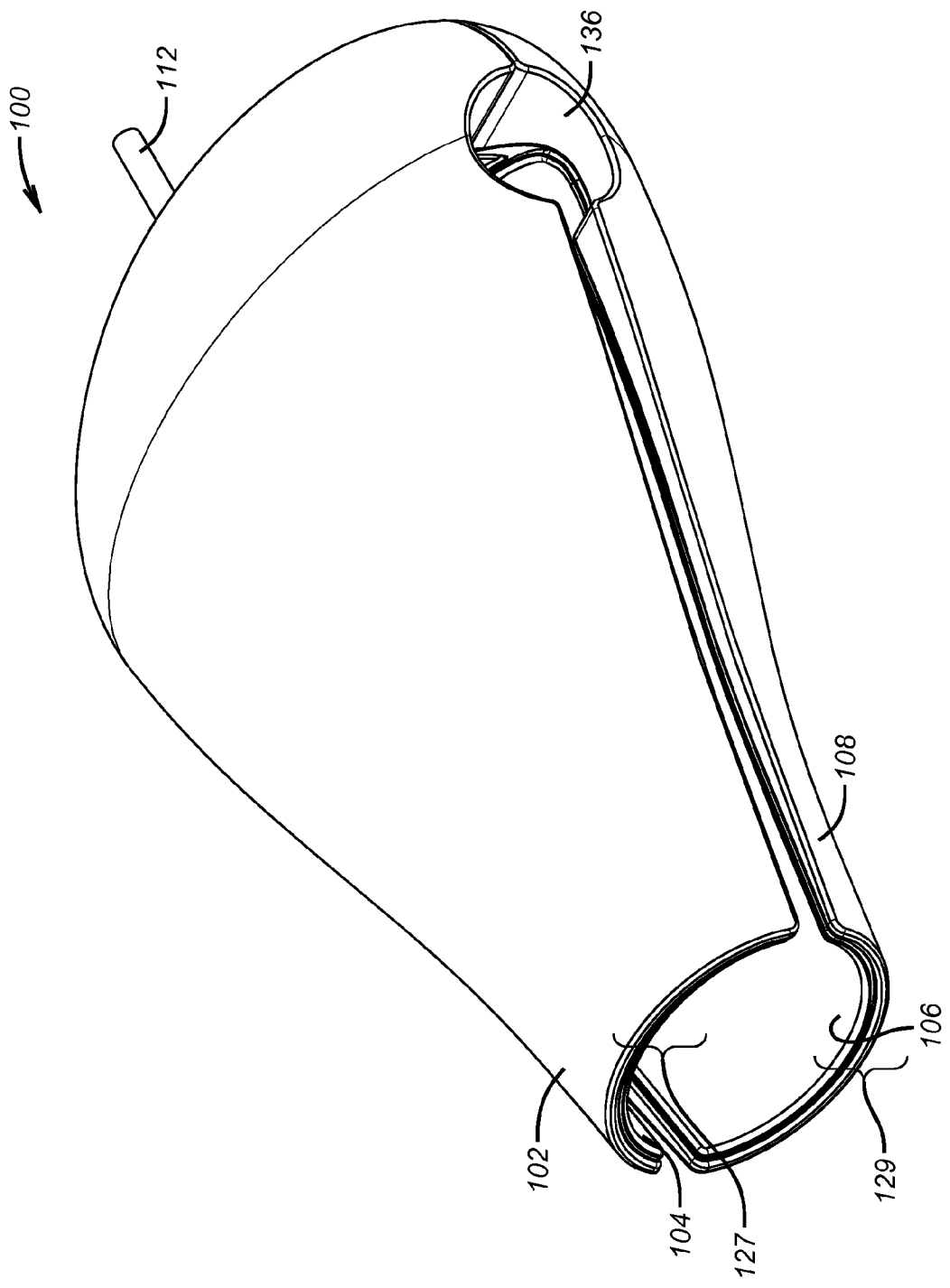
FIG. 1 is a perspective view of an assembled exemplary embodiment.

Specific details described herein, including what is stated in the Abstract, are in every case a non-limiting description and exemplification of embodiments representing concrete ways in which the concepts of the invention may be practiced. This serves to teach one skilled in the art to employ the present invention in virtually any appropriately detailed system, structure or manner consistent with those concepts. Reference throughout this specification to "an exemplary embodiment" means that a particular feature, structure, or characteristic described in connection with the embodiment is included in at least one exemplary embodiment of the present invention. Thus, the appearances of the phrase "in an exemplary embodiment" in various places throughout this specification are not necessarily all referring to the same embodiment. Furthermore, the particular features, structures, or characteristics may be combined in any suitable manner in one or more embodiments. It will be seen that various changes and alternatives to the specific described embodiments and the details of those embodiments may be made within the scope of the invention. It will be appreciated that one or more of the elements depicted in the drawings can also be implemented in a more separated or integrated manner, or even removed or rendered as inoperable in certain cases, as is useful in accordance with a particular application. Because many varying and different embodiments may be made within the scope of the inventive concepts herein described and in the exemplary embodiments herein detailed, it is to be understood that the details herein are to be interpreted as illustrative and not as limiting the invention to that which is illustrated and described herein.

The various directions such as "upper," "lower," "back," "front," "transverse,", "vertical", "normal," "horizontal," "length," "width," "laterally", and so forth used in the detailed description of exemplary embodiments are made only for easier explanation in conjunction with the drawings. The components may be oriented differently while performing the same function and accomplishing the same result as the exemplary embodiments herein detailed embody the concepts of the invention, and such terminologies are not to be understood as limiting the concepts which the embodiments exemplify.

As used herein, the use of the word "a" or "an" when used in conjunction with the term "comprising" (or the synonymous "having" or "including") in the claims and/or the specification may mean "one," but it is also consistent with the meaning of "at least one" and "one or more than one."

In addition, as used herein, the term "connected" means joined to or placed into communication with, either directly or through intermediate components.

In accordance with the present invention, exemplary embodiments of an uterine clamp are described for stemming or stopping bleeding of a hemorrhagic uterus. The clamp comprises a pair of inflatable bladders nested in a pair of rigid shells shaped and sized to fit the anterior and posterior of a uterus without impinging on the uterine horns on placement of the shells in mirrored spaced opposition to one another, one in front of and the other behind the broad ligament supporting the uterus. A releasable interlock for the shells includes at least one latch on an upper end of one shell and at least one latch catch in the upper end of the other shell for releasably interlocking the opposed shells in front of and behind the broad ligament anteriorly and posteriorly against the uterus for inflation of the bladders to compress the uterus anteriorly and posteriorly.

In accordance with this invention, a method of compressing a uterus to stem or stop hemorrhagic bleeding is provided. The method comprises (a) providing a pair of inflatable bladders nested in a pair of rigid shells shaped and sized to fit the anterior and posterior of a uterus without impinging on the uterine horns and having a releasable interlock comprising at least one latch on an upper end of one shell and at least one latch catch in the upper end of the other shell, (b) placing the shells with nested bladders in mirrored spaced opposition to one another in front of and behind the broad ligament supporting the uterus, (c) releasably interlocking the opposed shells in front of and behind the broad ligament anteriorly and posteriorly against the uterus, and (d) inflating the bladders to compress the uterus anteriorly and posteriorly.

In an exemplary embodiment, a uterine clamp comprises a pair of rigid shells each comprising a proximal concavely hemi-cupped base and a horizontally interiorly concave distal portion extend along a length of the shell from the base to an extremity. The distal portions of the shells are sized to fit the anterior and posterior of a uterus on placement of the shells in mirrored spaced opposition to one another in front of and behind the broad ligament supporting the uterus. The bases have a body sufficient relative to the distal portions of the shells to rigidly cantilever the distal portions. The shape of the shells may be generally hemi-pyriform. A pair of inflatable bladders shaped for nesting in the respective shells nest in the shells. Each nested bladder has an inflation conduit accessible exteriorly of the shells. In an exemplary embodiment, a uterine clamp includes an aperture in each shell, suitably, in an embodiment, in the base of the shell, for passage of the inflation conduit exteriorly of the shells. In an exemplary embodiment, the inflation conduit includes a pressure regulator remote from the clamp for extra-corporeally controlling the pressure imparted to the bladder. Each shell and nested bladder has a recess on both lateral sides adjacent the shell base such that when the two shells and nested bladders are placed in mirrored spaced opposition to one another in front and behind the broad ligament adjacent the uterus, the recesses form unclosed lateral surrounds around the uterine horns and included anatomy. A releasable interlock comprises a latch in the base of one shell and a latch catch in the base of the other shell for releasably interlocking the opposed shells in front of and behind the broad ligament anteriorly and posteriorly against the uterus for inflation of the bladders to compress the uterus anteriorly and posteriorly.

In an exemplary embodiment, the latch in the base of one shell comprises a mating male latch and the latch catch in the base of the other shell comprises a mating female catch.

In an exemplary embodiment, the male latch and female latch catch are parallel to the length of the shells.

In an exemplary such embodiment the male latch comprises resilient shanks horizontally extending from the latch base (i.e., a longitudinal direction parallel to the length of the shells). The shanks terminate in heads sloping from a crown to a chin and face laterally outward. The longitudinal direction in which the shanks project is a direction opposite the direction in which the distal portion of the shell extends. In an exemplary such embodiment in which a female latch catch is parallel to the length of the shells, the female catch comprises an opening horizontally passing through the latch catch base in the same direction as the shanks project. The opening exits to an exterior surface of the latch catch base. The opening has an interior dimension effective to admit the crowns of the heads and slide the heads along the slopes from crown to chin to pinch the heads closer together enough to pass the heads completely through the opening and to release the pinch on exit of the heads from the opening and catch the chins against the exterior surface.

In an exemplary embodiment of the latter type, the male latch may further comprise a flange normal to the latch base and transverse to the length of the shell with a horizontal rib protruding therefrom in a direction opposite the direction in which the distal portion extends. In this exemplary embodiment, the shanks project from the rib in the direction of the protrusion. In this exemplary embodiment the female latch catch further comprises a horizontal recess in the latch catch base transverse to the length of the shell for lodging the male rib therein. The opening for receipt of the shanks is set into the recess for lodging the rib.

In an exemplary embodiment, the female latch catch is spring biased to a latched state. The female latch spring may also have a spring bias for an unlatched state. By "spring bias" is meant that a spring acts to apply force to maintain a certain state in opposition to an external force or return the mechanism to a certain state once the external force is removed.

In an exemplary embodiment the male latch and female latch catch are normal to the length of the shells.

In an exemplary such embodiment the male latch comprises a plurality of resilient shanks vertically projecting from the latch base body (i.e., a direction normal to the length of the shells) and terminating in heads having a chin, and the female latch catch comprises one of more vertical hollow(s) in the latch catch base body. The hollow(s) are aligned and sized to receive the heads of the shanks. In an exemplary embodiment, the hollows may take the form of a plurality of wells. In an exemplary embodiment, the hollow may take the form of a slot. A horizontally translatable slide has an edge in contact with a horizontally deformable spring and is translatable transversely to the hollow(s) on deformation or elastic return of the spring. The slide is shaped to admit the male heads and shanks into the hollow(s) when the slide is pushed from a latching position to an unlatching position, and to capture the heads in the hollow(s) when the slide is translated back to a latching position.

In an exemplary embodiment, the slide is translational in the direction of the length of the shell. In this type embodiment, the heads may include a ramp having a surface sloping from a crown top to a chin base, and the female latch catch may further comprise a slide cover covering the slide. The slide cover has holes aligned and shaped to pass the heads. The ramp surfaces are adapted to contact an edge of the slide opposite an edge of the slide in contact with the spring to push the slide against the spring, allowing the heads to ramp past the slide into the hollow(s), such that when the ramp passes below the slide, the spring translates the slide in a direction opposite the direction in which the distal portions of the shells extend, capturing the shanks and interlocking the shells.

In this latter embodiment, the edge of the slide opposite the edge in contact with the spring may be sloped where the ramp surfaces contact the edge. This slope may be parallel to the ramp surface.

In an exemplary embodiment in which the slide is translational in the direction of the length of the shell, a plurality of fasteners may fasten the slide cover to the latch catch base and form posts retaining the latch slide within a predetermined range of translation.

In the exemplary embodiments in which the slide is translational in the direction of the length of the shell, the edge of the slide opposite the edge in contact with the spring and not where the ramp surfaces contact the edge may include a horizontal projection protruding beyond the latch catch body, wherein to disconnect the shells, the projection is pushed to translate the slide past the captured heads in the hollow(s), freeing the heads from restraint by the slide and allowing the two shells to be pulled apart.

In an exemplary embodiment, the slide is reciprocally translational transversely to the length of the shell of which the female latch catch base is part. The male latch comprises a plurality of shanks vertically projecting from the latch base body and terminating in heads having a chin. The female latch catch comprises a vertical hollow in the form of a slot in the latch catch base. The slot is transverse to the length of the shell of which the female latch catch base is part and is aligned and sized to receive the heads of said shanks. A horizontally translatable slide having an edge in contact with a horizontally deformable spring translates transversely in the slot on deformation or elastic return of the spring. The slide is shaped to admit the male heads and shanks into the slot when the slide is in an unlatching position and to capture the heads when the slide is translated to a latching position. In an embodiment, the slide has recesses formed in stepped heights in the bottom of the slide. A taller of the stepped heights is too high to catch the chins of latch heads introduced into the slot. Positioning the slide so that this height is over the latch heads of the male assembly unlatches the male assembly from the female assembly. A shorter of the stepped heights is sized low enough to catch the chins of heads introduced into the slot. Positioning the slide so that this lower height is over the chins of the latch heads captures the heads in the slot and interlocks the male and female assemblies together.

Figure 2:
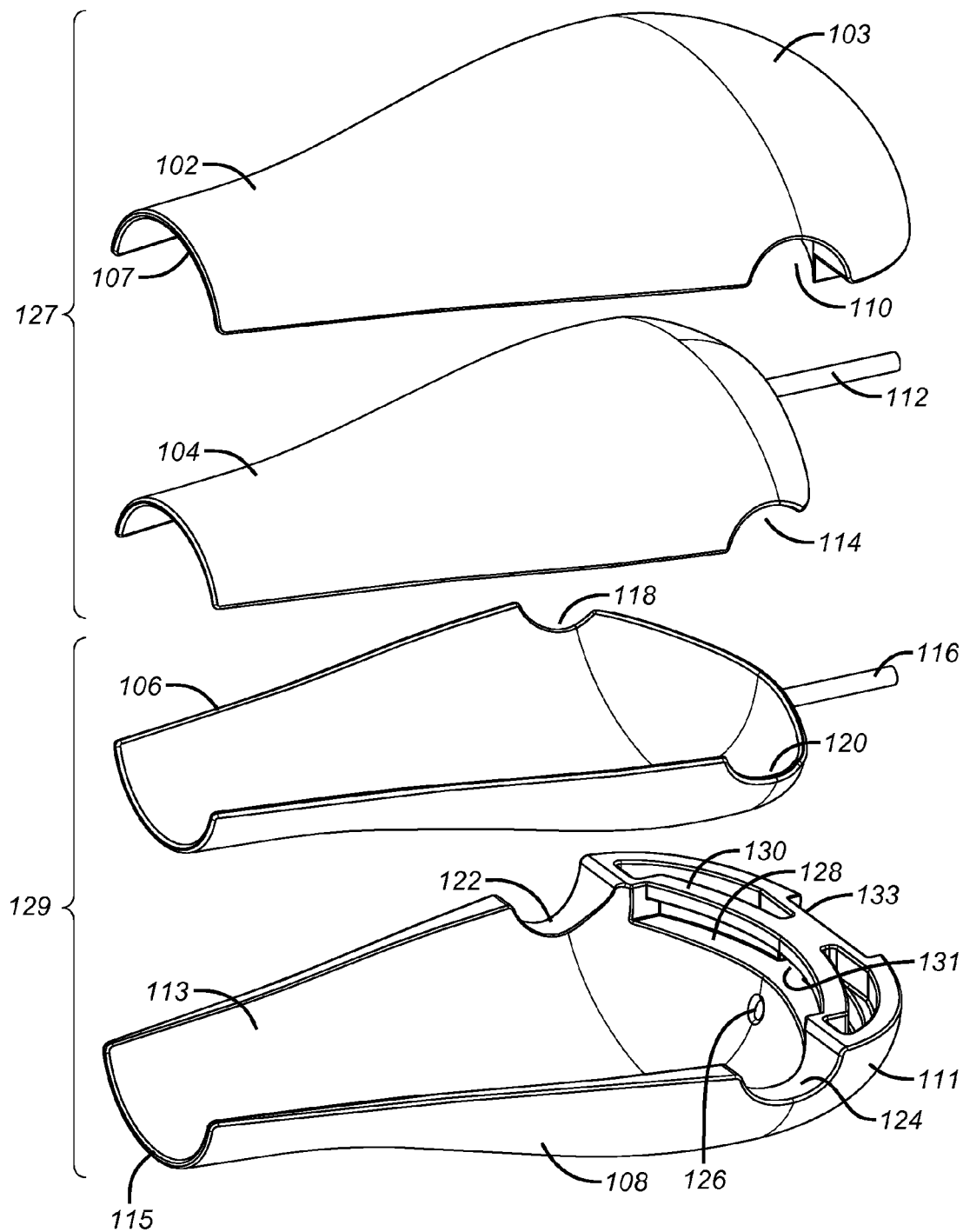
FIG. 2 is an exploded view of the embodiment of FIG. 1.

Referring now to the figures for a detailed description of several embodiments that accord with the invention, FIG. 1 illustrates the assembly of an exemplary embodiment 100 of a uterine clamp in which upper and lower assemblies 127, 129 are interlocked by a male latch and female latch catch that are parallel to the length of the assemblies, as will be described. FIG. 2 illustrates an exploded view of embodiment 100 showing the component parts. An upper rigid concave shell 102 generally hemi-pyriform in shape is preferably a thermoplastic with a lateral recess generally in the form of a semicircle 110. The other and opposite lateral recess 109 of shell 102 is viewable in FIG. 3. Shell 102 includes a proximal concavely hemi-cupped base 103 and a horizontal interiorly concave distal portion 105 extending along a length of shell 102 from base 103 to an extremity 107. Lateral recesses 109, 110 are adjacent base 103. A flexible, concave, generally hemi-pyriform bladder 104 is shaped to nest inside of shell 102 resulting in the upper assembly 127. Bladder 104 has an inflation conduit 112 protruding from one end accessible exteriorly of shell 102. Conduit 112 permits gas to be introduced from the outside of the body of a patient into bladder 104, permitting bladder 104 to expand within shell 102. Like shell 102, bladder 104 has a lateral recess 114. Recess 114 aligns to lateral recess 110 in shell 102. The other and opposite lateral recess of bladder 104 is not viewable in FIG. 2.

Figure 5:
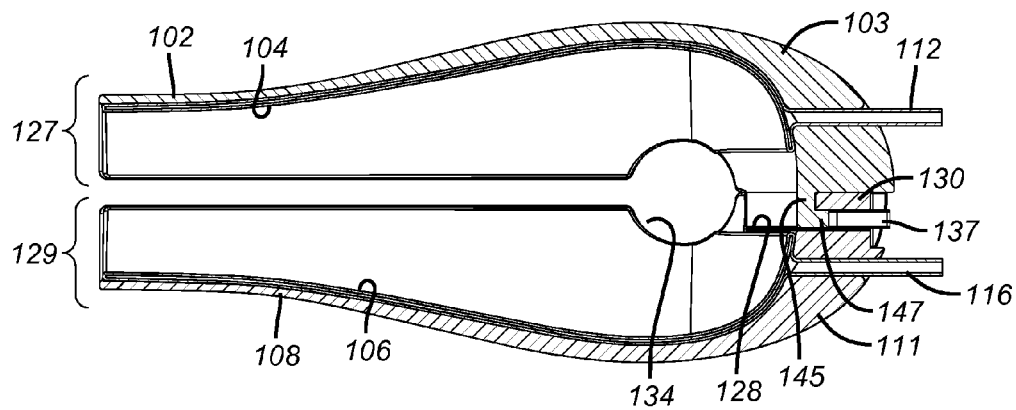
FIG. 5 is a vertically sectioned side view of the embodiment of FIG. 1.

Lower bladder 106 is an approximate mirror image of upper bladder 104 including an inflation conduit 116, for similar gas introduction to lower bladder 106 just as inflation conduit 112 does for upper bladder 104. Lower bladder 106 is also shaped to nest inside of lower, rigid, generally hemi-pyriform shaped shell 108, resulting in lower assembly 129. Lower shell 108 is also preferably made of a thermoplastic and includes a proximal concavely hemi-cupped base 111 and a horizontal interiorly concave distal portion 113 extending along a length of shell 108 from base 111 to an extremity 115. Lateral recesses 118 and 120 of lower bladder 106 are generally semi-circular and generally conform to lateral recesses 122 and 124 of lower shell 108. When shells 102 and 108 and included nested bladders 104, 106 are placed in mirrored spaced opposition to one another, the recesses form unclosed lateral surrounds 134, 136 (FIGS. 1, 5). Lower shell 108 has an aperture 126 in base 111 so the inflation conduit 116 of bladder 106 may pass through it. Upper shell 102 has a similar aperture 138 for inflation conduit 112 of bladder 104 viewable in FIG. 3. In lower shell 108 there is a horizontal recess 128 in base 111 transverse to the length of shell 108 under bridge 130. Inset in recess 128 is an opening 131 horizontally passing through the base 111 and exiting to an exterior surface 133 of base 111 of shell 108.

Figure 3:
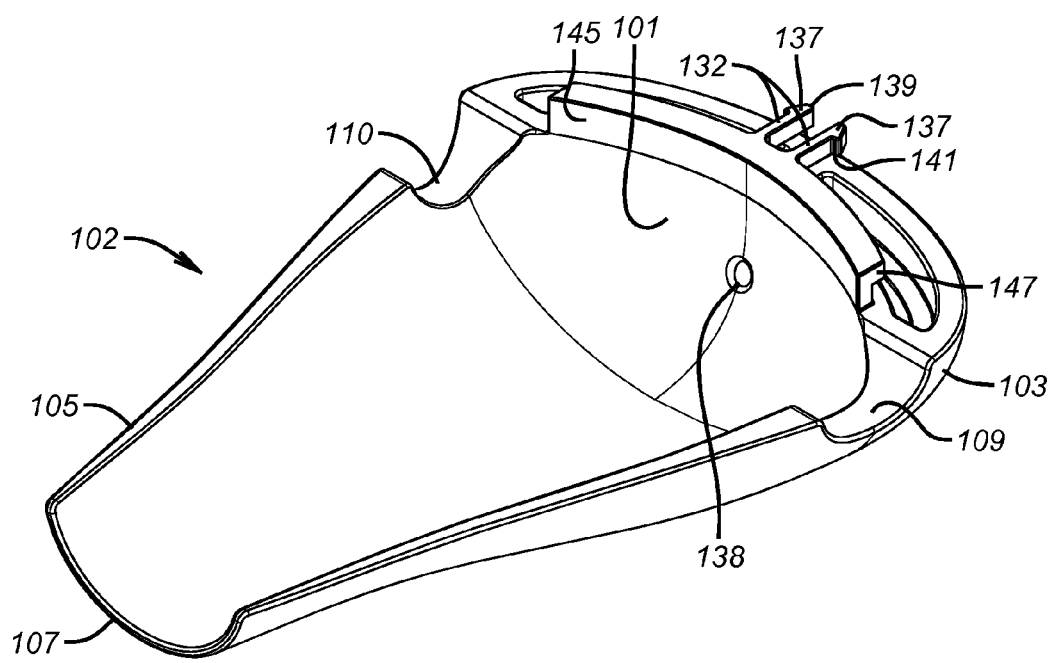
FIG. 3 is an inverted view of the top shell of the embodiment from FIG. 2.

FIG. 3 illustrates the underside view of upper shell 102 from FIG. 2. Shell 102 has a pair of resilient shanks 132 horizontally extending from base 103 forming a component of a male mating latch comprising shanks 132 and heads 137 protruding from shell 102 in a longitudinal direction opposite the direction in which distal portion 105 extends. Shanks 132 terminate in heads 137 sloping from crown 139 to chin 141 and face laterally outwards. Another component of the male mating latch is flange 145 normal to the latch base 103 at body portion 101 and transverse to the length of shell 102. Flange 145 has a horizontal rib 147 protruding from it in a direction opposite the direction in which distal portion 105 extends. Shanks 132 project from rib 147 in the direction of the protrusion of rib 147. The shanks are used for releasably interlocking the upper shell assembly 127 to the lower shell assembly 129. There is an aperture 138 where inflation conduit 112 of bladder 104 may pass through.

Figure 4:
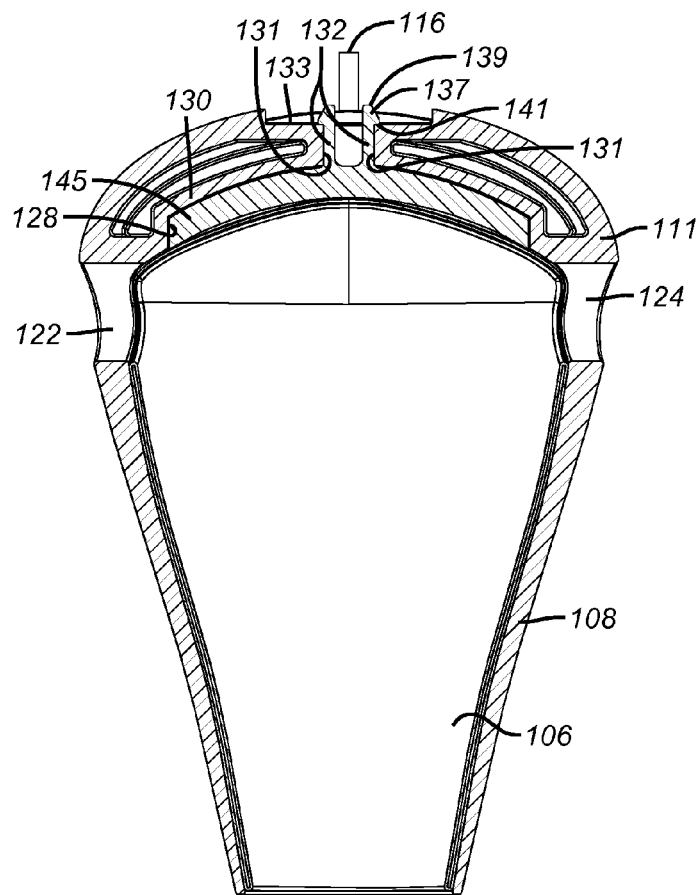
FIG. 4 is a horizontally sectioned top view of the embodiment of FIG. 1 illustrating the latching of the top and bottom assemblies.

FIG. 4 illustrates a sectioned top view of embodiment 100. Shanks 132 are designed such that their length versus their individual width provide shanks 132 with side-to-side flexure. When interlocking top assembly 127 to bottom assembly 129, heads 137 of shanks 132 of top shell 102 are inserted through the recess 128 into opening 131 of shell 108. Opening 131 has an interior dimension effective to admit the crowns 139 of heads 137 and slide heads 137 along the slopes from crowns 139 to chins 141 to pinch heads 137 inwardly and closer together enough to pass heads 137 completely through opening 131. Once heads 137 have passed through opening 131 the pinch of the heads forced by the interior dimension of opening 131 is released and the chins 141 of the heads are allowed to engage the outside rim of opening 131 at the exterior surface 133 of base 111, catching the latch provided by shanks 132 and latching top assembly 127 to bottom assembly 129. This union is supported by a rib 147 lodging in recess 128 under bridge 130 with flange 145 braced by the side of bridge 130. The overall body of latch base 103 of upper shell 102 inclusive of flange 145 and ribs 147 and the overall body of latch catch base 111 of lower shell 106 inclusive of depth of recess 128, bridge 130 and opening 131 contribute to platforms providing a rigid cantilever respectively of distal portions 105 and 113 of assemblies 127 and 129 when shells 102 and 108 are latched together.

FIG. 5 illustrates a sectioned side view of embodiment 100. Upper assembly 127 is shown with its upper shell 102 and upper bladder 104. Similarly, lower assembly 129 is shown with lower shell 108 and lower bladder 106. Inflation conduits 112 and 116 can seen to be exiting the upper 127 and lower 129 assemblies to the right. Head 137 of shank 132 projects from rib 147 of flange 145. Bridge 130 lodges rib 147 in place. Flange 145 rests in recess 128.

In use, the sterilized lower assembly 129 of the embodiment is placed behind the uterine broad ligament posterior to the uterus and sterilized upper assembly 127 is placed in front of the uterine broad ligament anterior to the uterus in mirrored spaced opposition to lower assembly 129 before the two assemblies are latched together. This placement is such that uterine horns and included anatomy (including the fallopian tubes to the uterus and round ligament) enclosed in the uterine broad ligaments that laterally support the uterus in the pelvis pass through the matching opposed unclosed lateral surrounds 134, 136 adjacent the latch base 103 and latch catch base 111. Further, this placement is such that the cervix of the uterus projects through the matched opposing extremities 107 and 115 of respective distal portions 105, 113 of shells 102, 108. Once anatomically placed, the inflation conduits 112 and 116 extend outside the body. The distal ends of the inflation conduits 112 and 116 are then connected to a pressure source and the bladders 104 and 106 can then be preferentially inflated causing pressure on the uterus, but not on the fallopian tubes. The rigidly cantilevered assemblies 127 and 129 are such that the pressure formed in bladders 104 and 106 does not deflect distal portions 105, 113 of shells 102, 108 materially outwardly, so they remain generally parallel and the pressure consequently is directed inwardly to the uterus. Suitably the inflation conduits are fitted with a pressure regulator. Pressure on the uterus by bladders 104 and 106 is regulated to exceed the arterial blood pressure that feeds the uterus, generally up to about 250 mmHg, and this will cause hemostasis. Removal of the uterine clamp of embodiment 100 generally follows the above procedure in reverse. Pressure is removed to collapse bladders 104, 106, the heads 137 of the shanks 132 protruding from opening 131 are manually pinched together, the shanks 132 are pulled from the opening 131 and the ribs 145 at the same time are pulled from recess 128, releasing the interlock of the two assemblies for removal of clamp 100 from the patient.

Figure 6:
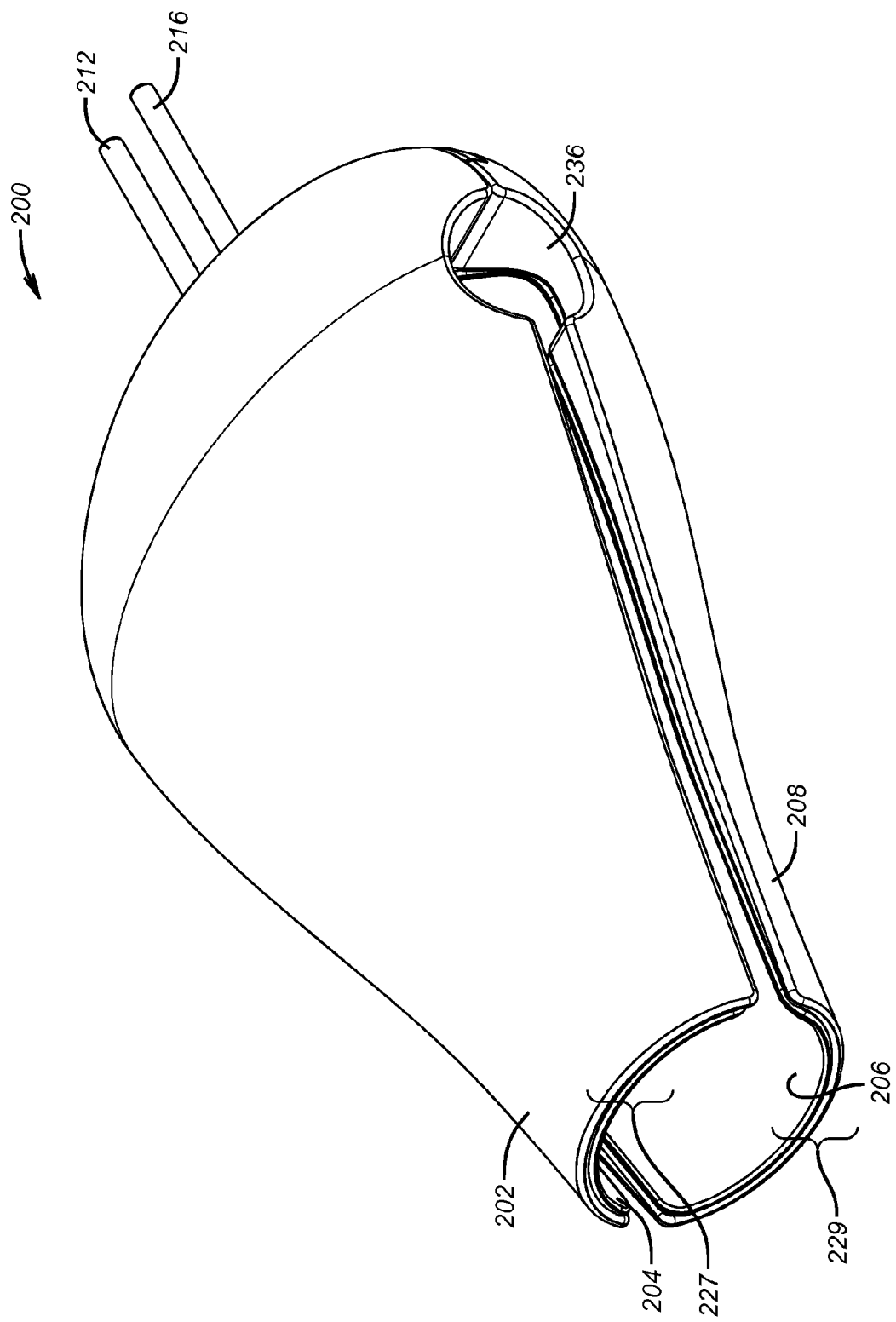
FIG. 6 is an overview of another exemplary embodiment.

FIG. 6 illustrates an exemplary embodiment of another uterine clamp assembly 200 in accordance with the invention. In most instances the reference numerals in FIGS. 6-10 correspond to the reference numerals for analogous parts in the exemplary embodiment of FIGS. 1-5, plus 100, e.g., 105 for the embodiment of FIGS. 1-5 is 205 for the embodiment of FIGS. 6-11.

Figure 7:
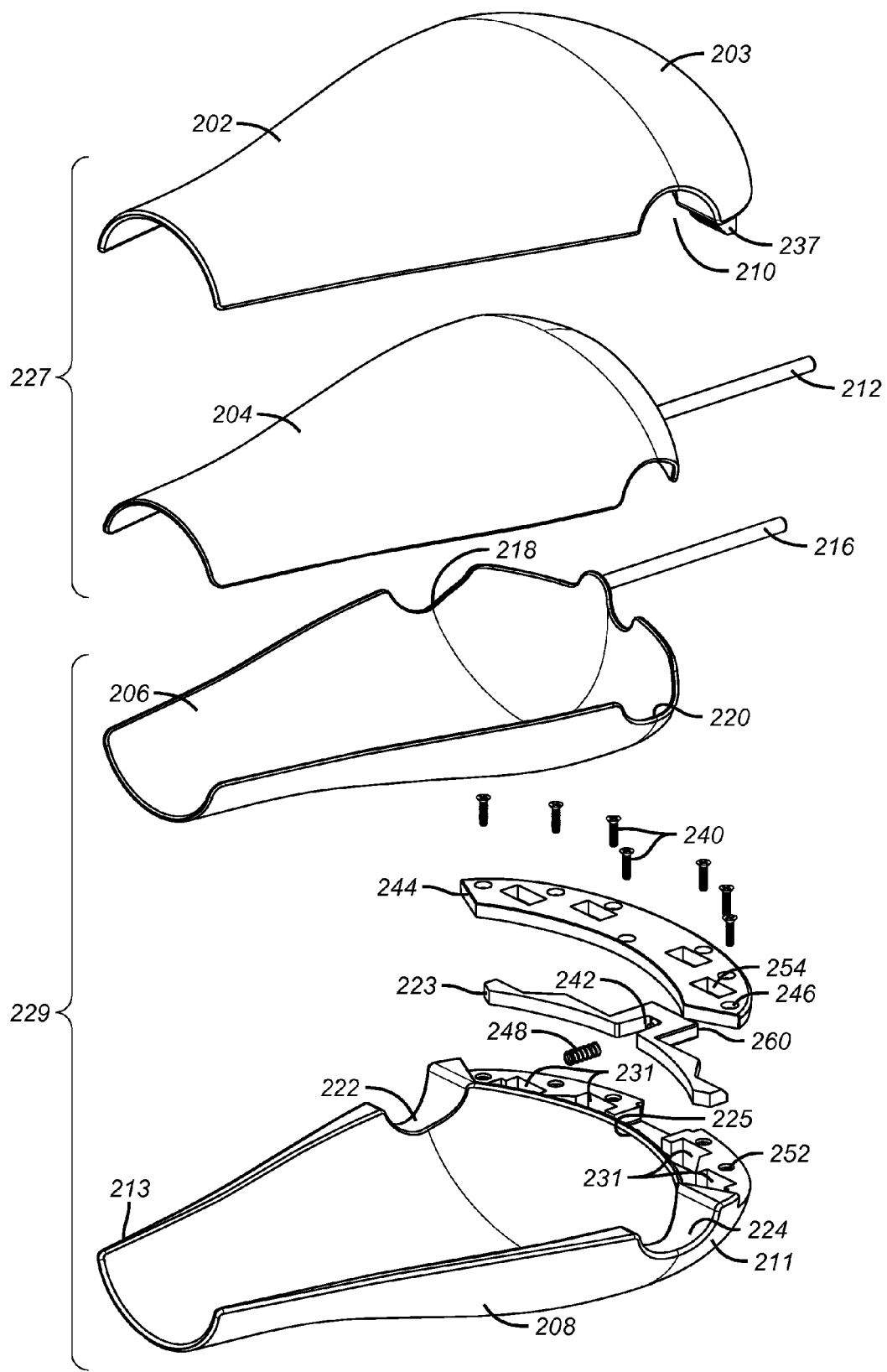
FIG. 7 is an exploded view of the embodiment shown in FIG. 6, showing the individual components which make up the embodiment.

In this exemplary embodiment 200, the male latch comprising shanks 232 and heads 237 on the base 203 of shell 202 at body portion 201 and the female latch catch on the base 211 of shell 208 are normal to the length of the shells. FIG. 7 illustrates the exploded view of 200, showing the component parts. The upper, rigid, shell 202, of generally hemi-pyriform shape, is preferably thermoplastic with a lateral recess generally in the form of a semicircle 210. The other and opposite lateral recess 209 of shell 202 is viewable in FIG. 8. Shell 202 includes a proximal concavely hemi-cupped base 203 and a horizontal interiorly concave distal portion 205 extending along a length of shell 202 from base 203 to an extremity 207. Lateral recesses 209, 210 are adjacent base 203. Shell 202 has a plurality of shanks 232 vertically projecting from the latch base body 203 and terminating in heads 237 having a chin 241 (better seen in FIG. 8). An upper flexible bladder 204, also of generally hemi-pyriform shape, is designed to nest on to the inside of the upper shell 202. The upper bladder 204 has an inflation conduit 212 protruding from the end of it which permits gas to be introduced to the upper bladder permitting the bladder to expand inwardly from upper shell 202. Together they form upper assembly 227. Lower, flexible, generally hemi-pyriform shaped bladder 206 is an approximate mirror image to upper bladder 204. Lower bladder 206 also has an inflation conduit 216, for gas introduction. Lower bladder 206 is also designed to nest on the inside of lower shell 208. Lower shell 208 is also preferably made of a thermoplastic and includes a proximal concavely hemi-cupped base 211 and a horizontal interiorly concave distal portion 213 extending along a length of shell 208 from base 211 to an extremity. Lateral recesses 218 and 220 of lower bladder 206 are generally semi-circular and generally conform to lateral recesses 222 and 224 of lower shell 208. When shells 202 and 208 and included nested bladders 204, 206 are placed in mirrored spaced opposition to one another the recesses form unclosed lateral surrounds 234, 236 (FIGS. 6, 10). Lower shell 208 has a variety of components which assemble to it on the latch catch base 211. Latch catch base 211 of shell 208 has a plurality of vertical wells 231 in the body of latch catch base 211. Wells 231 are aligned and sized to receive heads 237 of shanks 232. Latch catch slide 223 has a notch 242. Spring 248 fits into notch 242 in latch catch slide 223 and is positioned on a horizontal centering post 219 (see FIG. 9) when assembled so that one edge of slide 223 in the form of notch 242 with its centering post 219 contacts spring 248. The other end of spring 248 is positioned on a centering post 217 extending horizontally from vertical transverse wall 225 which is an integral part of base 211 of lower shell 208. The function of spring 248 is to put outward force on the latch catch slide 223, whose function is discussed later. The edge 221 of latch catch slide opposite notch 242 includes a horizontal projection 260 protruding beyond the latch catch body. Latch catch slide 223 is sandwiched between bottom shell 208 and latch catch slide cover 244. Latch catch slide cover 244 has holes 254 in it aligned and shaped to pass heads 237. A plurality of fasteners 240 are positioned to clear holes 246 of latch slide cover 244 and fasten into holes 252 of lower shell 208. Fasteners 240 fasten latch catch slide cover 244 to latch catch base 211 and form posts retaining latch catch slide 223 within a slideway gap 262 (FIGS. 11A, 11B) between latch catch slide cover 244 and latch catch base 211. Together, lower shell 208 inclusive of wells 231, lower bladder 206, latch slide cover 244, latch slide 223, spring 248 and fasteners 240 form lower assembly 229.

Figure 8:
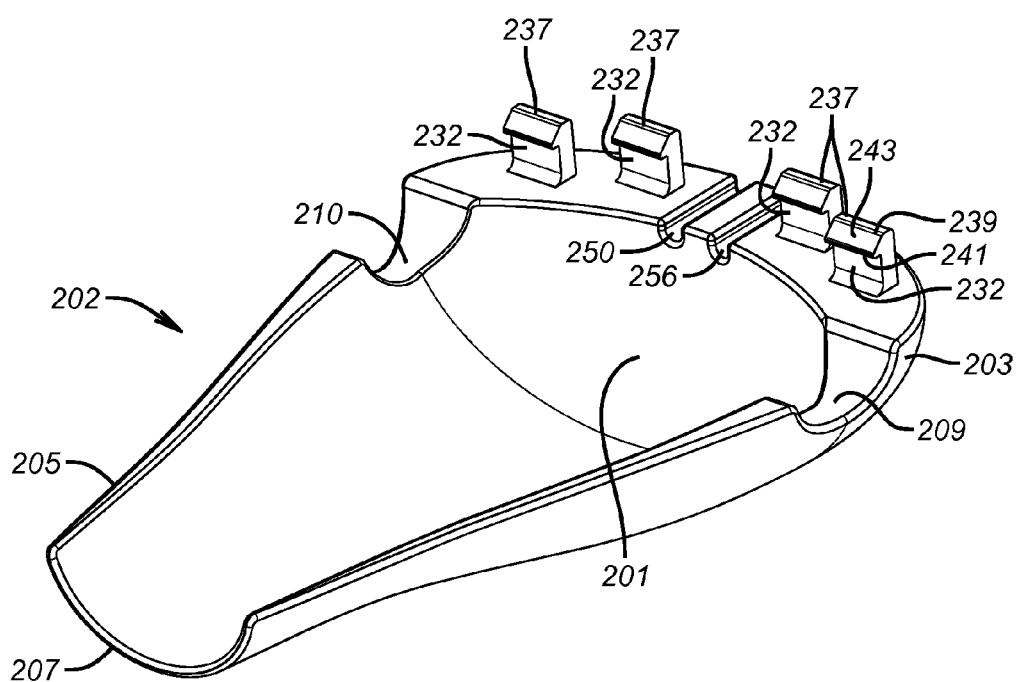
FIG. 8 is an inverted view of the top shell of the embodiment illustrated in FIG. 7, showing its component parts.

FIG. 8 illustrates the reverse side, or inside of upper shell 202 shown in FIG. 7. Upper shell 202 has two longitudinal slots 250 and 256 to permit inflation conduits 212 and 216 to exit the upper assembly 227. As mentioned, a plurality of shanks 232 vertically project from latch base body 203 on the upper shell 202 and terminate in heads 237 having a chin 241. Heads 237 include a ramp 243 having a surface sloping from crown top 239 to a chin base 241.

Figure 9:
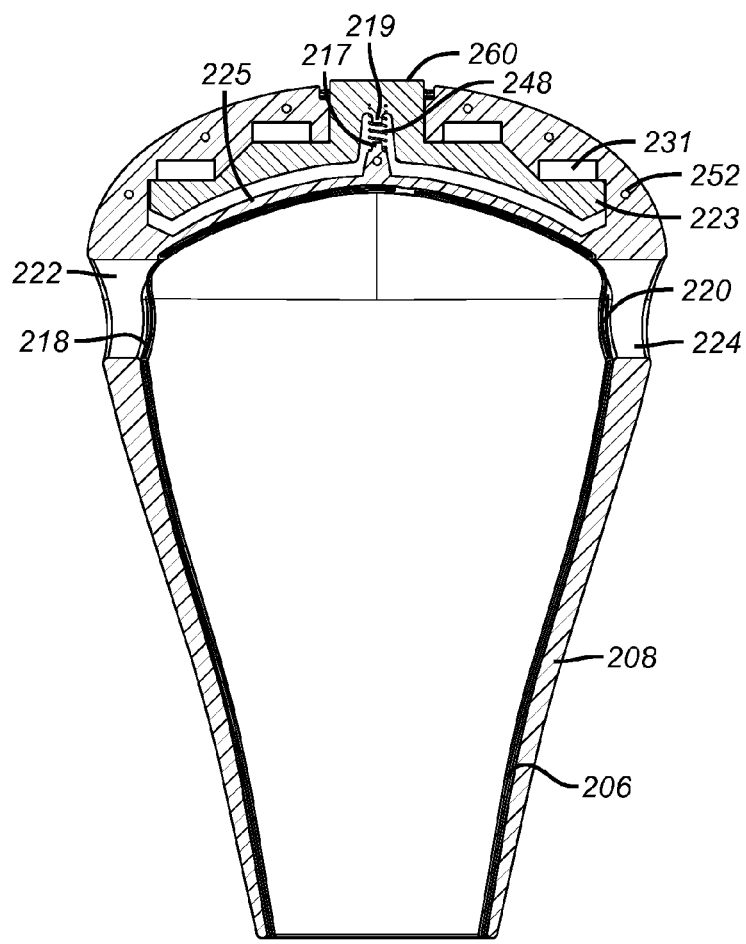
FIG. 9 is a horizontally sectioned top view of the embodiment of FIG. 6 illustrating some of the components of the assembly.
Figure 10:
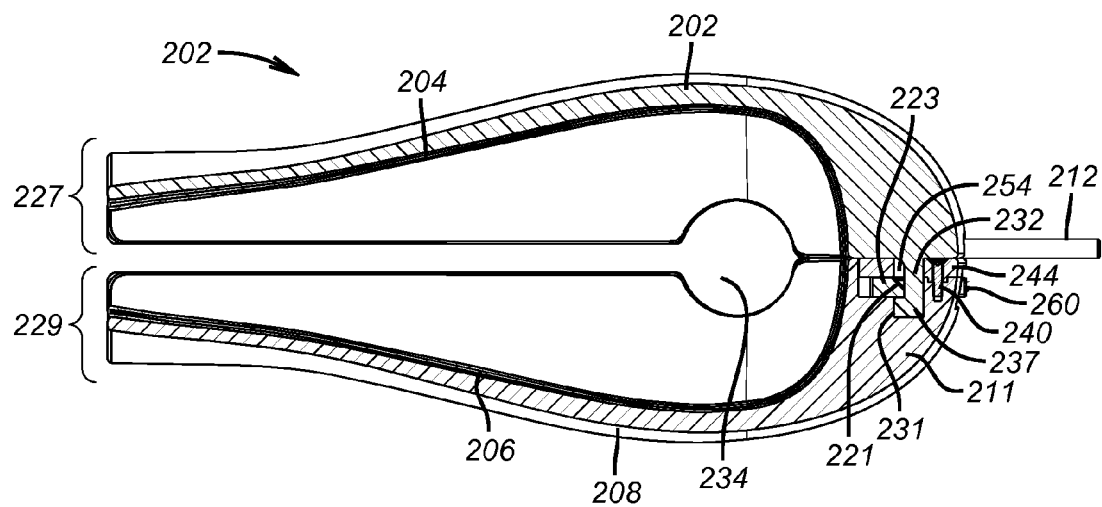
FIG. 10 is a vertically sectioned side view of the embodiment of FIG. 6.

FIG. 9 illustrates a sectional top view of assembled lower shell 229 without the latch slide cover 244. Lower shell 208 has lower bladder 206 nested within it. Spring 248 is shown contained within notch 242 in the latch catch slide 223 positioned on centering posts 217 and 219. Slide 223 is shown partially covering wells 231 under the extension force of spring 248. Slide projection 260 is depicted protruding exteriorly of the exterior surface of base 211 of shell 208.

FIG. 10 illustrates a sectioned side view of embodiment 200. Upper shell assembly 227 is shown with its upper shell 202 and nested upper bladder 204. Similarly, lower assembly 229 is shown with lower shell 208 and its nested bladder 206. Inflation conduits 212 and 216 can seen to be exiting the assembly to the right. Similar to embodiment 100, lateral surrounds 234, 236 are formed by the upper and lower shells, 202 and 208 and upper and lower bladders 204 and 206 to permit pressurization of the uterus without compressing the fallopian tubes. Head 237 of shank 232 projects through holes 254 of latch catch slide cover 244, captured by latch catch slide 223. Fasteners 240 fasten latch slide cover 244 to latch catch base 211.

Figure 11A:
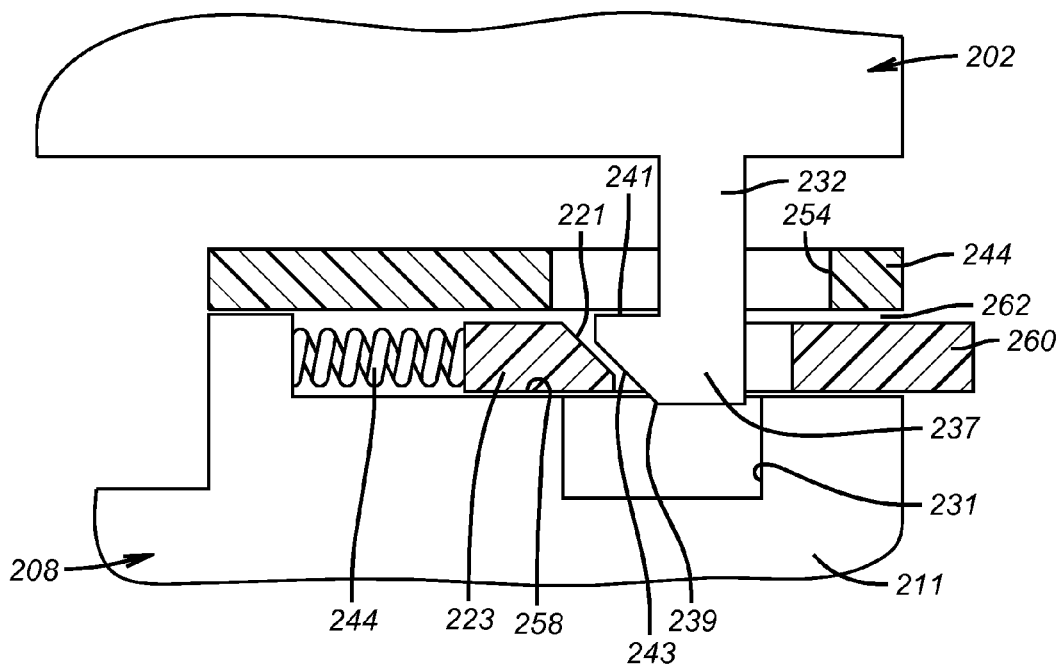
FIG. 11A is a close up longitudinally vertically sectioned schematic side view of the latching mechanism of the embodiment of FIG. 6 in an unlatched state.
Figure 11B:
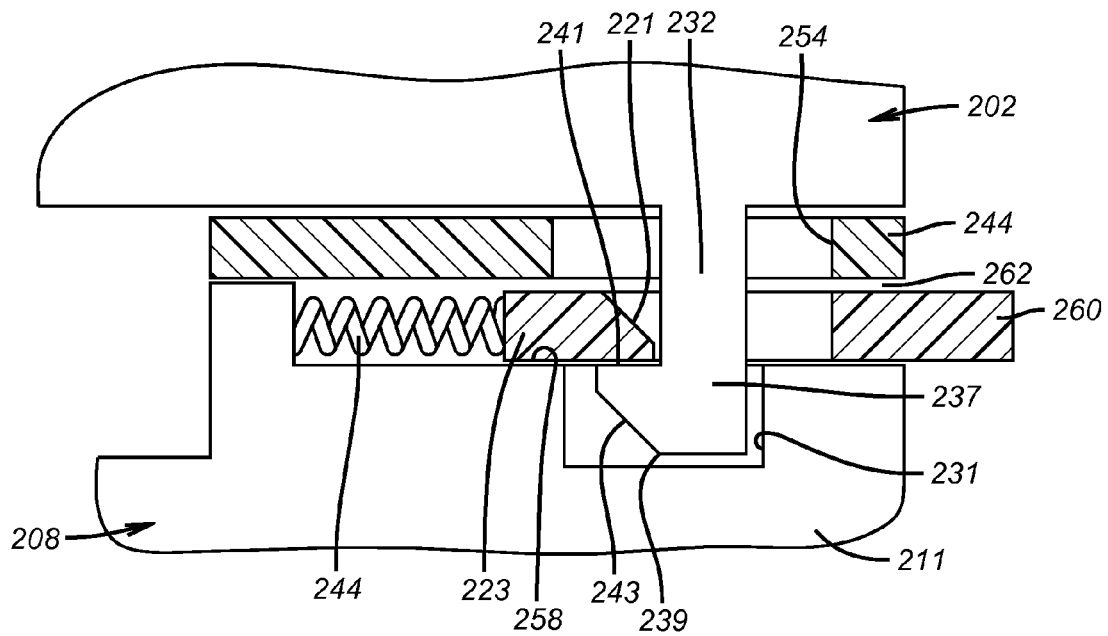
FIG. 11B is a close up longitudinally vertically sectioned schematic side view of the latching mechanism of the embodiment of FIG. 6 in the latched state.

FIGS. 11A and 11B schematically show close up views of the engaging area of the sectioned side view of FIG. 10. FIG. 11A shows top shell 202 with integral shanks 232 and heads 237 moving into the lower shell assembly 229. As the shanks 232 move into the assembly 229 containing the lower shell 202, the heads 237 pass through apertures 254 in the latch catch slide cover 244 and the ramp surfaces 243 of heads 237 contact the inclined edge 221 of latch catch slide 223. The incline of edge 221 is substantially parallel to the slope of ramp 243. As this engagement occurs, the ramps 243 of heads 237 sliding down the incline of edge 221 push latch catch slide 223 (in this view, to the left) against spring 248, permitting upper shell 202, shanks 232 and heads 237 to continue their downward motion, allowing the heads to slide into the wells 231. FIG. 11B shows the top assembly 227 and bottom assembly 229 of embodiment 200 releasably locked together. Once the chin 241 of head 237 passes below the lower horizontal surface 258 of latch catch slide 223, spring 248 is free to force latch catch slide 223 in a direction opposite the direction in which distal portion 215 of shell 208 extends (in this view, to the right), capturing shanks 232 and locking assembly 227 and assembly 229 together. Pushing projection 260 of latch catch slide 223 to the left against spring 248 translates slide 223 past heads 237 in wells 231, freeing heads 237 from restraint by latch catch slide 223, unlatching assembly 227 and therefore permitting it to be detached from assembly 229. The overall body of latch base 203 of upper shell 202 and the overall body of latch catch base 211 of lower shell 206 contribute to platforms providing a rigid cantilever respectively of distal portions 205 and 213 of assemblies 227 and 229 when shells 202 and 208 are latched together.

In use, the procedure, cantilevering aspects and inflation of the bladder against the uterus of the embodiment 200 has the advantages of and follows the procedure described above for embodiment 100.

Figure 12A:
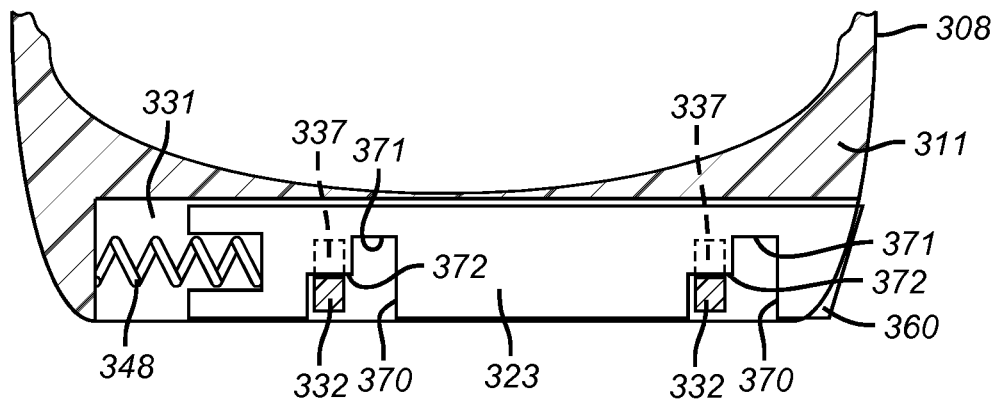
FIG. 12A is close up of a transversely horizontally sectioned schematic top view of another latching mechanism in the latched state.
Figure 12B:
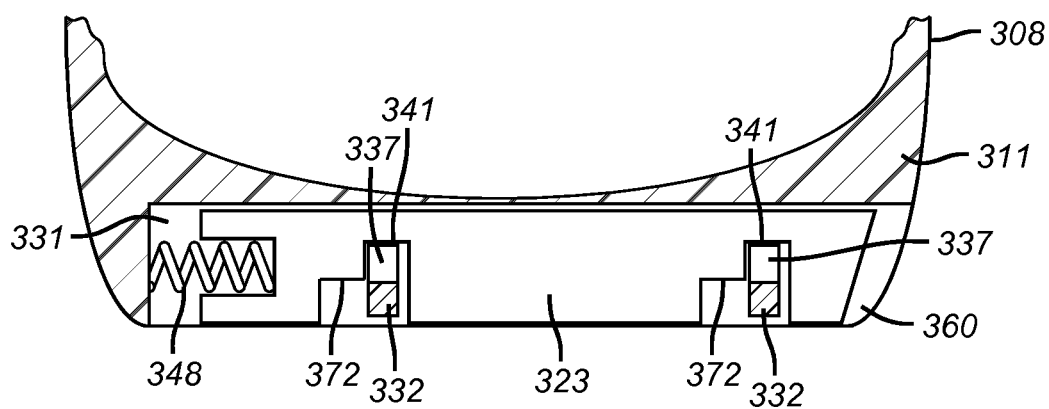
FIG. 12B is a close up transversely horizontally sectioned schematic top view of the latching mechanism in the unlatched state, for an alternative embodiment.

In most instances the reference numerals in FIGS. 12A and 12B correspond to the reference numerals for analogous parts in the exemplary embodiment of FIGS. 6-11, plus 100, e.g., 332, 337 for the embodiment of FIGS. 12A, 12B corresponds generally to 232, 237 respectively, for the embodiment of FIGS. 6-11.

FIG. 12 illustrates schematically the latching mechanism of another exemplary embodiment in which the male latch comprising shanks 332 and heads 337 on a latch base of a first shell of an assembly analogous to assembly 227 but for the manner of interlock and the female latch catch 323 on the base 311 of a second shell 308 are normal to the length of the shells. In this mechanism, latch catch slide 323 translates in a hollow in the form of a slot 331 transverse to the length of the shells on deformation or elastic return of spring 348. The hollow(s) optionally can be hollows in the form of wells as the embodiments of FIGS. 6-11. Slot 331 is aligned and sized to receive heads 337 of shanks 332 that project vertically from the latch base of an the assembly analogous to assembly 227 but for the manner of interlock. The portion of such assembly apart from the latching mechanism is not shown but will be understood from the foregoing description of assembly 227. Similarly, the portion of a mating assembly apart from the latching mechanism is not shown but will be understood from the foregoing description of assembly 229. Latch catch slide 323 includes horizontal notches 370 in a side of the slide. Notches 370 have stepped depths 371, 372. The depth 371 of notch 370 is greater than the horizontal cross section distance across shank 332 and head 337 to chin 341 and thus sufficient for latch catch slide 323 not to catch chin 341 of head 337 and trap head 337 when slide 323 is present over chin 341. The depth 372 of notch 370 is sufficient to accept shank 332 but not head 337 and therefore shallower than depth 371 sufficiently for latch catch slide 323 to catch chin 341 of head 337 and trap head 337 when moved over chin 341 by translation of latch catch slide 323.

In the view of FIGS. 12A, 12B, translation of latch catch slide 323 in slot 331 is respectively left-to-right and right-to-left. In the view of FIG. 12B, latch catch slide 323 is pushed right-to-left by pressing on slide projection 360, translating slide 323 over slot 331 transversely to the length of assembly 329 and deforming spring 348. Assembly 327 is positioned to introduce heads 337 projecting from shanks 332 into slot 331 of assembly 329. The depths 371 of notches 370 are too deep for slide 323 to catch chins 341 of heads 237. In the view of FIG. 12A, projection 360 of slide 323 is released, and the elastic return of spring 348 has translated slide 323 left-to-right over slot 331 to move slide 323 with the shallower depths 372 of notches 370 over chins 341 of heads 337. Slide 323 therefore catches chins 341 and traps heads 337. This latches heads 337 and hence assembly 327 to assembly 329.

The above-disclosed subject matter is to be considered illustrative, and not restrictive. The appended claims are intended to cover all modifications, enhancements, and other embodiments that fall within the true scope of the present invention. To the maximum extent allowed by law, the present invention is to be determined by the broadest permissible interpretation of the following claims and their equivalents, unrestricted or limited by the foregoing detailed descriptions of exemplary embodiments of the invention.

The invention claimed is:

1. A uterine clamp for stemming or stopping bleeding of a hemorrhagic uterus, comprising a pair of inflatable bladders nested in a pair of rigid shells each comprising a proximal base and a distal portion extending from said proximal base along a length of the shell from the base to an extremity, said shells being shaped and sized to circumferentially fit around the anterior and posterior of a uterus without impinging on the uterine horns on placement of the shells in mirrored spaced opposition to one another immediately in front of and behind the broad ligament supporting the uterus, said shells each having a releasable interlock comprising at least one latch only on said proximal base of one shell and at least one latch catch only in said proximal base of the other shell for releasably interlocking the opposed shells in front of and behind the broad ligament against the uterus, each said proximal base comprising a body sufficient relative to the distal portion of the shell to provide a platform rigidly cantilevering said distal portion when the proximal bases of the shells are interlocked, said bladders each nesting in the cantilevered distal portion from adjacent said proximal base for inflation of the bladders to compress the uterus anteriorly and posteriorly between said cantilevered distal portions.

2. The uterine clamp of claim 1 in which the said at least one latch in the base of one shell comprises a mating male latch and in which the said at least one latch catch in the base of the other shell comprises a mating female catch.

3. The uterine clamp of claim 2 in which the male latch and female latch catch are parallel to the length of the shells.

4. The uterine clamp of claim 3 in which
the male latch comprises resilient shanks horizontally extending from a latch base and terminating in heads sloping from a crown to a chin and facing laterally outwardly, the shanks projecting in a longitudinal direction opposite the direction in which said distal portion extends, and wherein the female latch catch comprises an opening horizontally passing through a latch catch base in the same direction as the shanks project and exiting to an exterior surface of the latch catch base, the opening having an interior dimension effective to admit the crowns of the heads and slide the heads along the slopes to pinch the heads together enough to pass the heads completely through the opening and release the pinch to catch the chins against the exterior surface.

5. The uterine clamp of claim 4 in which the male latch further comprises a flange normal to the latch base and transverse to the length of the shell with a horizontal rib protruding therefrom in a direction opposite the direction in which said distal portion extends, wherein said shanks project from the rib in the direction of the protrusion of the rib, and wherein the female latch catch further comprises a horizontal recess in the latch catch base transverse to the length of the shell for lodging said male rib therein, said recess insetting said opening for receipt of said shanks.

6. The uterine clamp of claim 2 in which said male latch and said female latch catch are normal to the length of the shells.

7. The uterine clamp of claim 6 in which said female latch catch is spring biased to a latched state whether the male latch is present and interlocking or not.

8. The uterine clamp of claim 7 in which said male latch comprises: a plurality of shanks vertically projecting from the base of one shell and terminating in heads having a chin, and wherein said female latch catch comprises: one or more vertical hollows in the base of the other shell, said hollow(s) being aligned and sized to receive said heads of said shanks, and a horizontally translatable slide having an edge in contact with a horizontally deformable spring, said slide translating transversely to said hollow(s) on deformation or on elastic return of the spring, said slide being shaped to admit the male heads and shanks into the hollow(s) when the slide is in an unlatching position and to capture the heads when the slide is translated to a latching position.

9. The uterine clamp of claim 8 in which the slide is translational in the direction of the length of the shell.

10. The uterine clamp of claim 9 in which the heads include a ramp having a surface sloping from a crown top to a chin base, and wherein said female latch catch further comprises a slide cover covering said slide, said slide cover having holes aligned and shaped to pass said heads, said ramp surfaces adapted to contact an edge of the slide opposite said edge of the slide in contact with the spring to push the slide against the spring, allowing the heads to ramp past the slide into the hollow(s), such that when the ramp passes below the slide, the spring translates the slide in a direction opposite the direction in which said distal portions extend, capturing the shanks and interlocking the shells.

11. The uterine clamp of claim 10 in which said edge of the slide opposite the edge in contact with the spring is sloped where the ramp surfaces contact the edge, such slope being parallel to the ramp surface.

12. The uterine clamp of claim 11 in which the edge of the slide opposite the edge in contact with the spring and not where the ramp surfaces contact the edge includes a horizontal projection protruding beyond the latch catch body, wherein to disconnect the shells, the projection is pushed to translate the slide past captured heads in the hollow(s), freeing the heads from restraint by the slide and allowing the two shells to be detached.

13. The uterine clamp of claim 8 in which the slide is translational transversely to the length of the shell.

14. The uterine clamp of claim 13 wherein said latch catch slide has notches formed in stepped depths in a side of the slide, the deeper of the stepped heights being too deep to catch the chins of latch heads introduced into the hollow(s), and the shallower of the stepped depths being shallow enough for the slide to catch the chins of heads introduced into the hollow(s) on translation of the slide over the hollow(s).

15. A uterine clamp for stemming or stopping bleeding of a hemorrhagic uterus, comprising:

a pair of rigid shells each comprising a proximal concavely hemi-cupped base and a horizontal interiorly concave distal portion extending from said base along a length of the shell from the base to an extremity, the distal portions of the shells having lateral margins and being shaped and sized to circumferentially fit around the anterior and posterior of a uterus on placement of the shells in mirrored spaced opposition to one another immediately in front of and behind the broad ligament supporting the uterus, said shells each having a releasable interlock comprising at least one latch only on said proximal base of one shell and at least one latch catch only in said proximal base of the other shell for releasably interlocking the opposed shells in front of and behind the broad ligament against the uterus, each said proximal base comprising a body sufficient relative to the distal portion of the shell to provide a platform rigidly cantilevering said distal portion when the proximal bases of the shells are interlocked, and a pair of inflatable bladders each shaped for nesting in the shells, each bladder having an inflation conduit accessible exteriorly of the shells, for inflation of the bladders to compress the uterus anteriorly and posteriorly between said cantilevered distal portions, each shell and bladder having lateral recesses vertical relative to the horizontal length of said distal portion of the shell and adjacent only the base such that when the two shells and the bladders nesting in the shells are placed in mirrored spaced opposition to one another immediately in front and behind the broad ligament adjacent the uterus, the recesses form unclosed lateral surrounds around the uterine horns and anatomy included therein.

16. The uterine clamp of claim 15 in which the inflation conduit includes a pressure regulator remote from the clamp.

17. The uterine clamp of claim 15 including an aperture in each shell for passage of the inflation conduit exteriorly of the shells.

18. The uterine clamp of claim 17 in which the aperture is in said base of each of said shell.

19. An organ clamp for stemming or stopping organ bleeding, comprising a pair of inflatable bladders nested in a pair of rigid shells each comprising a proximal base and a distal portion extending from said proximal base along a length of the shell from the base to an extremity, said shells being shaped and sized to fit the anterior and posterior of the organ without impinging on any anatomical vessels extending into or from the organ on placement of the shells in mirrored opposition to one another in front of and behind the organ, said shells each having a releasable interlock comprising at least one latch only on said proximal base of one shell and at least one latch catch only in said proximal base of the other shell for releasably interlocking the opposed shells in front of and behind the organ anteriorly and posteriorly against the organ, each said proximal base comprising a body sufficient relative to the distal portion of the shell to provide a platform rigidly cantilevering the distal portion when the proximal bases of the shells are interlocked, said bladders each nesting in the cantilevered distal portion from adjacent said proximal base for inflation of the bladders to compress the organ anteriorly and posteriorly between said cantilevered distal portions.

20. A uterine clamp for stemming or stopping bleeding of a hemorrhagic uterus, comprising:
  a pair of rigid shells comprising a proximal concavely hemi-cupped base and a horizontal interiorly concave distal portion extending along a length of the shell from the base to an extremity, each said distal portion being cantilevered from each said proximal base, the bases having a body sufficient relative to the distal portions to rigidly cantilever the distal portions, the distal portions of the shells being sized to fit the anterior and posterior of a uterus on placement of the shells in mirrored spaced opposition to one another in front of and behind the broad ligament supporting the uterus,
  a pair of inflatable bladders shaped for nesting in the shells, each bladder having an inflation conduit accessible exteriorly of the shells,
  each shell and bladder having lateral recesses adjacent the base such that when the two shells and the bladders nesting in the shells are placed in mirrored spaced opposition to one another in front and behind the broad ligament adjacent the uterus, the recesses form unclosed lateral surrounds around the uterine horns and anatomy included therein, and
  a releasable interlock for releasably interlocking the opposed shells in front of and behind the broad ligament anteriorly and posteriorly against the uterus for inflation of the bladders to compress the uterus anteriorly and posteriorly between said cantilevered distal portions, said interlock comprising a mating male latch in the base of one shell and a mating female latch catch in the base of the other, said female latch catch being shell spring biased to a latched state, said male latch comprising a plurality of shanks vertically projecting from the base of one shell and terminating in heads having a chin and including a ramp having a surface sloping from a crown top to a chin base, and said female latch catch comprising one or more vertical hollows in the base of the other shell, said hollow(s) being aligned and sized to receive said heads of said shanks, and a horizontally translatable slide having an edge in contact with a horizontally deformable spring, said slide translating in the direction of the length of the shell transversely to said hollow(s) on deformation or on elastic return of the spring, said slide being shaped to admit the male heads and shanks into the hollow(s) when the slide is in an unlatching position and to capture the heads when the slide is translated to a latching position, said ramp surfaces adapted to contact an edge of the slide opposite said edge of the slide in contact with the spring to push the slide against the spring, allowing the heads to ramp past the slide into the hollow(s), such that when the ramp passes below the slide, the spring translates the slide in a direction opposite the direction in which said distal portions extend, capturing the shanks and interlocking the shells, said female latch catch further comprising a slide cover covering said slide, said slide cover having holes aligned and shaped to pass said heads, a plurality of fasteners fastening said slide cover to the latch catch base wherein the fasteners are posts retaining the latch slide within said latch catch base.

\* \* \* \* \*